(12) United States Patent
Lee et al.

(10) Patent No.: US 9,145,583 B2
(45) Date of Patent: Sep. 29, 2015

(54) MULTI-SPOT METAL-CAPPED NANOSTRUCTURE ARRAY NUCLEIC ACID CHIP FOR DIAGNOSIS OF CORNEAL DYSTROPHY AND PREPARATION METHOD THEREOF

(75) Inventors: Sang Yup Lee, Daejeon (KR); So Young Yoo, Seoul (KR); Do Kyun Kim, Daejeon (KR); Tae Jung Park, Daejeon (KR); Jung Kuk Yun, Chungcheongbuk-do (KR); Gene Lee, Gyeonggi-do (KR)

(73) Assignee: AVELLINO CO., LTD., Seoul (KR)

( * ) Notice: Subject to any disclaimer, the term of this patent is extended or adjusted under 35 U.S.C. 154(b) by 368 days.

(21) Appl. No.: 13/391,167

(22) PCT Filed: Aug. 18, 2010

(86) PCT No.: PCT/KR2010/005452
§ 371 (c)(1),
(2), (4) Date: Jun. 7, 2013

(87) PCT Pub. No.: WO2011/021846
PCT Pub. Date: Feb. 24, 2011

(65) Prior Publication Data
US 2014/0243222 A1     Aug. 28, 2014

(30) Foreign Application Priority Data

Aug. 18, 2009  (KR) .................. 10-2009-0076300

(51) Int. Cl.
*C12Q 1/68* (2006.01)
*C12M 1/36* (2006.01)
*B82Y 30/00* (2011.01)

(52) U.S. Cl.
CPC .............. *C12Q 1/6837* (2013.01); *B82Y 30/00* (2013.01); *C12Q 1/6883* (2013.01);
(Continued)

(58) Field of Classification Search
CPC .... C12Q 1/6837; C12Q 1/6883; B82Y 30/00; B02J 2219/00509
USPC ................................................. 435/6.1, 287.2
See application file for complete search history.

(56) References Cited

U.S. PATENT DOCUMENTS 6,331,276 B1 * 12/2001 Takei et al. ................. 422/82.09
2003/0176650 A1 * 9/2003 Grosse et al. ................. 530/350
(Continued)

FOREIGN PATENT DOCUMENTS

EP    2 019 309 A2    1/2009
JP    2006-250668 A    9/2006
(Continued)

OTHER PUBLICATIONS

Carl T. Wittwer et. al., Real-Time Multiplex PCR Assays, 2001, 13 pgs., Salt Lake City, Utah.
(Continued)

*Primary Examiner* — Betty Forman
(74) *Attorney, Agent, or Firm* — Morgan, Lewis & Bockius LLP

(57) ABSTRACT

A multi-spot metal-capped nanostructure array nucleic acid chip for diagnosing corneal dystrophy, and more particularly to a multi-spot metal-capped nanostructure array nucleic acid chip capable of employing LSPR (localized surface plasmon resonance) optical properties, a preparation method thereof, and a multi-spot metal-capped nanostructure array nucleic acid chip for diagnosing BIGH3 gene mutations, which can diagnose various corneal dystrophies. The metal-capped nanostructure array nucleic acid chip can be combined with analysis devices, including a light source, a detector, a spectrophotometer and a computer, to provide an LSPR optical property-based optical biosensor, and the use of the multi-spot metal-capped nanostructure array nucleic acid chip for diagnosing BIGH3 gene mutations allows the simultaneous diagnosis of various corneal dystrophies that are genetic ocular diseases.

7 Claims, 6 Drawing Sheets

(52) U.S. Cl.
CPC .................. *B01J 2219/00509* (2013.01); *B01J 2219/00608* (2013.01); *B01J 2219/00612* (2013.01); *B01J 2219/00614* (2013.01); *B01J 2219/00621* (2013.01); *B01J 2219/00637* (2013.01); *B01J 2219/00648* (2013.01); *B01J 2219/00722* (2013.01); *C12Q 2600/158* (2013.01)

(56) References Cited

U.S. PATENT DOCUMENTS

| | | | | |
|---|---|---|---|---|
| 2004/0217345 | A1* | 11/2004 | Boland et al. | 257/40 |
| 2004/0263853 | A1* | 12/2004 | Hill et al. | 356/445 |
| 2006/0038990 | A1* | 2/2006 | Habib et al. | 356/301 |
| 2006/0066249 | A1* | 3/2006 | Wark et al. | 315/111.21 |
| 2007/0254296 | A1* | 11/2007 | Jiang et al. | 435/6 |
| 2007/0274895 | A1* | 11/2007 | Jesih et al. | 423/462 |
| 2008/0174775 | A1* | 7/2008 | Moskovits et al. | 356/301 |
| 2009/0073447 | A1* | 3/2009 | Dahint et al. | 356/445 |
| 2011/0053794 | A1* | 3/2011 | Zhang | 506/9 |

FOREIGN PATENT DOCUMENTS

| | | |
|---|---|---|
| JP | 2009-523442 A | 7/2007 |
| JP | 2009-045057 A | 1/2009 |
| WO | WO 2007/083928 A1 | 7/2007 |

OTHER PUBLICATIONS

Feb. 18, 2015 European Search Report of application No. 14186678.0.

* cited by examiner

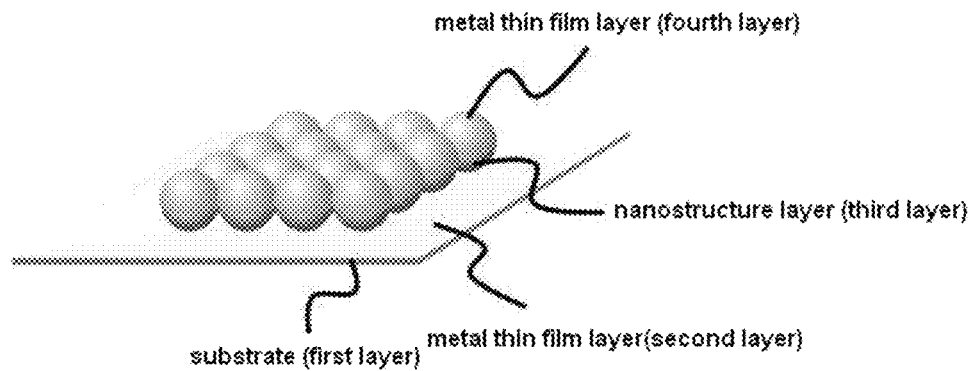

Metal-capped nanostructure array nucleic acid chip for diagnosing corneal dystrophy

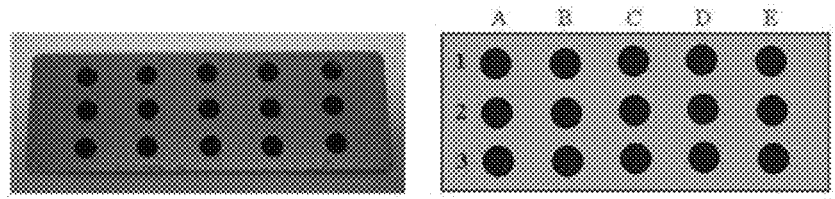

15 Multi-spot metal-capped nanostructure array nucleic acid chip for diagnosing corneal dystrophy

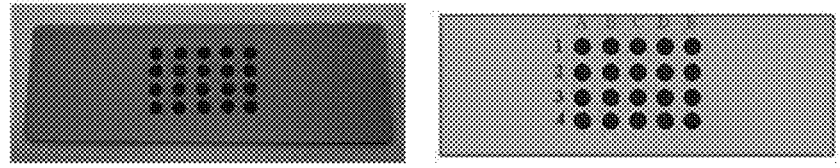

20 Multi-spot metal-capped nanostructure array nucleic acid chip for diagnosing corneal dystrophy

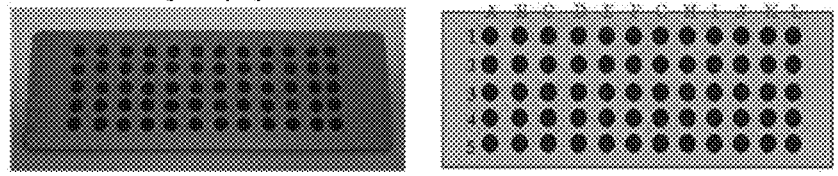

60 Multi-spot metal-capped nanostructure array nucleic acid chip for diagnosing corneal dystrophy

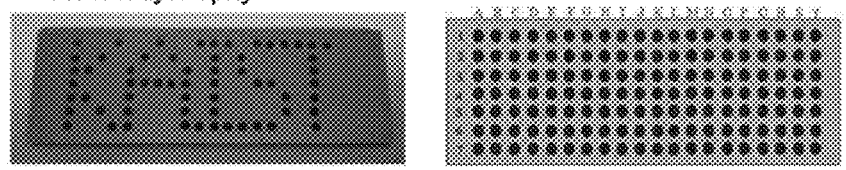

140 Multi-spot metal-capped nanostructure array nucleic acid chip for diagnosing corneal dystrophy

FIG. 1

SEQUENCE LISTING

<160> NUMBER OF SEQ ID NOS: 46

<210> SEQ ID NO 1
<211> LENGTH: 20

```
<212> TYPE: DNA
<213> ORGANISM: Artificial sequence
<220> FEATURE:
<223> OTHER INFORMATION: primer

<400> SEQUENCE: 1 agcagccta ccactctcaa                                              20

<210> SEQ ID NO 2
<211> LENGTH: 18
<212> TYPE: DNA
<213> ORGANISM: Artificial sequence
<220> FEATURE:
<223> OTHER INFORMATION: primer

<400> SEQUENCE: 2
caggcctcgt tgctaggg                                               18

<210> SEQ ID NO 3
<211> LENGTH: 20
<212> TYPE: DNA
<213> ORGANISM: Artificial sequence
<220> FEATURE:
<223> OTHER INFORMATION: primer

<400> SEQUENCE: 3
ccccagaggc catccctcct                                             20

<210> SEQ ID NO 4
<211> LENGTH: 20
<212> TYPE: DNA
<213> ORGANISM: Artificial sequence
<220> FEATURE:
<223> OTHER INFORMATION: primer

<400> SEQUENCE: 4
ccgggcagac ggaggtcatc                                             20

<210> SEQ ID NO 5
<211> LENGTH: 20
<212> TYPE: DNA
<213> ORGANISM: Artificial sequence
<220> FEATURE:
<223> OTHER INFORMATION: primer

<400> SEQUENCE: 5
ctcgtgggag tataaccagt                                             20

<210> SEQ ID NO 6
<211> LENGTH: 20
<212> TYPE: DNA
<213> ORGANISM: Artificial sequence
<220> FEATURE:
<223> OTHER INFORMATION: primer

<400> SEQUENCE: 6
tgggcagaag ctccacccgg                                             20

<210> SEQ ID NO 7
<211> LENGTH: 27
<212> TYPE: DNA
<213> ORGANISM: Artificial sequence
<220> FEATURE:
<223> OTHER INFORMATION: primer

<400> SEQUENCE: 7
```

```
cattccagtg gcctggactc tactatc                                          27

<210> SEQ ID NO 8
<211> LENGTH: 23
<212> TYPE: DNA
<213> ORGANISM: Artificial sequence
<220> FEATURE:
<223> OTHER INFORMATION: primer

<400> SEQUENCE: 8
ggggccctga gggatcacta ctt                                              23

<210> SEQ ID NO 9
<211> LENGTH: 20
<212> TYPE: DNA
<213> ORGANISM: Artificial sequence
<220> FEATURE:
<223> OTHER INFORMATION: primer

<400> SEQUENCE: 9
ctgttcagta aacacttgct                                                  20

<210> SEQ ID NO 10
<211> LENGTH: 20
<212> TYPE: DNA
<213> ORGANISM: Artificial sequence
<220> FEATURE:
<223> OTHER INFORMATION: primer

<400> SEQUENCE: 10
ctctccacca actgccacat                                                  20

<210> SEQ ID NO 11
<211> LENGTH: 15
<212> TYPE: DNA
<213> ORGANISM: Artificial sequence
<220> FEATURE:
<223> OTHER INFORMATION: probe

<400> SEQUENCE: 11
acggaccgca cggag                                                       15

<210> SEQ ID NO 12
<211> LENGTH: 15
<212> TYPE: DNA
<213> ORGANISM: Artificial sequence
<220> FEATURE:
<223> OTHER INFORMATION: probe

<400> SEQUENCE: 12
acggaccaca cggag                                                       15

<210> SEQ ID NO 13
<211> LENGTH: 15
<212> TYPE: DNA
<213> ORGANISM: Artificial sequence
<220> FEATURE:
<223> OTHER INFORMATION: probe

<400> SEQUENCE: 13
acggacctca cggag                                                       15

<210> SEQ ID NO 14
<211> LENGTH: 15
<212> TYPE: DNA
<213> ORGANISM: Artificial sequence
```

```
<220> FEATURE:
<223> OTHER INFORMATION: probe

<400> SEQUENCE: 14
cacggaccgc acgga                                                  15

<210> SEQ ID NO 15
<211> LENGTH: 15
<212> TYPE: DNA
<213> ORGANISM: Artificial sequence
<220> FEATURE:
<223> OTHER INFORMATION: probe

<400> SEQUENCE: 15
cacggactgc acgga                                                  15

<210> SEQ ID NO 16
<211> LENGTH: 15
<212> TYPE: DNA
<213> ORGANISM: Artificial sequence
<220> FEATURE:
<223> OTHER INFORMATION: probe

<400> SEQUENCE: 16
gaccccccca atggg                                                  15

<210> SEQ ID NO 17
<211> LENGTH: 15
<212> TYPE: DNA
<213> ORGANISM: Artificial sequence
<220> FEATURE:
<223> OTHER INFORMATION: probe

<400> SEQUENCE: 17
gacccccaca atggg                                                  15

<210> SEQ ID NO 18
<211> LENGTH: 15
<212> TYPE: DNA
<213> ORGANISM: Artificial sequence
<220> FEATURE:
<223> OTHER INFORMATION: probe

<400> SEQUENCE: 18
agcatgctgg tagct                                                  15

<210> SEQ ID NO 19
<211> LENGTH: 15
<212> TYPE: DNA
<213> ORGANISM: Artificial sequence
<220> FEATURE:
<223> OTHER INFORMATION: probe

<400> SEQUENCE: 19
agcatgccgg tagct                                                  15

<210> SEQ ID NO 20
<211> LENGTH: 15
<212> TYPE: DNA
<213> ORGANISM: Artificial sequence
<220> FEATURE:
<223> OTHER INFORMATION: probe

<400> SEQUENCE: 20
gcaggactga cggag                                                  15
```

```
<210> SEQ ID NO 21
<211> LENGTH: 15
<212> TYPE: DNA
<213> ORGANISM: Artificial sequence
<220> FEATURE:
<223> OTHER INFORMATION: probe

<400> SEQUENCE: 21
gcaggacgga cggag                                                      15

<210> SEQ ID NO 22
<211> LENGTH: 15
<212> TYPE: DNA
<213> ORGANISM: Artificial sequence
<220> FEATURE:
<223> OTHER INFORMATION: probe

<400> SEQUENCE: 22
acagtctttg ctccc                                                      15

<210> SEQ ID NO 23
<211> LENGTH: 16
<212> TYPE: DNA
<213> ORGANISM: Artificial sequence
<220> FEATURE:
<223> OTHER INFORMATION: probe

<400> SEQUENCE: 23
acacagtcgc tcccac                                                     16

<210> SEQ ID NO 24
<211> LENGTH: 15
<212> TYPE: DNA
<213> ORGANISM: Artificial sequence
<220> FEATURE:
<223> OTHER INFORMATION: probe

<400> SEQUENCE: 24
cccacaaatg aagcc                                                      15

<210> SEQ ID NO 25
<211> LENGTH: 15
<212> TYPE: DNA
<213> ORGANISM: Artificial sequence
<220> FEATURE:
<223> OTHER INFORMATION: probe

<400> SEQUENCE: 25
cccacaagtg aagcc                                                      15

<210> SEQ ID NO 26
<211> LENGTH: 15
<212> TYPE: DNA
<213> ORGANISM: Artificial sequence
<220> FEATURE:
<223> OTHER INFORMATION: probe

<400> SEQUENCE: 26
cccacaaacg aagcc                                                      15

<210> SEQ ID NO 27
<211> LENGTH: 15
<212> TYPE: DNA
<213> ORGANISM: Artificial sequence
<220> FEATURE:
<223> OTHER INFORMATION: probe
```

```
<400> SEQUENCE: 27
cccacaagcg aagcc                                                    15

<210> SEQ ID NO 28
<211> LENGTH: 15
<212> TYPE: DNA
<213> ORGANISM: Artificial sequence
<220> FEATURE:
<223> OTHER INFORMATION: probe

<400> SEQUENCE: 28
cccacatctg aagcc                                                    15

<210> SEQ ID NO 29
<211> LENGTH: 15
<212> TYPE: DNA
<213> ORGANISM: Artificial sequence
<220> FEATURE:
<223> OTHER INFORMATION: probe

<400> SEQUENCE: 29
cccacatccg aagcc                                                    15

<210> SEQ ID NO 30
<211> LENGTH: 15
<212> TYPE: DNA
<213> ORGANISM: Artificial sequence
<220> FEATURE:
<223> OTHER INFORMATION: probe

<400> SEQUENCE: 30
cccacatcag aagcc                                                    15

<210> SEQ ID NO 31
<211> LENGTH: 15
<212> TYPE: DNA
<213> ORGANISM: Artificial sequence
<220> FEATURE:
<223> OTHER INFORMATION: probe

<400> SEQUENCE: 31
cccacatcgg aagcc                                                    15

<210> SEQ ID NO 32
<211> LENGTH: 16
<212> TYPE: DNA
<213> ORGANISM: Artificial sequence
<220> FEATURE:
<223> OTHER INFORMATION: probe

<400> SEQUENCE: 32
aaatgaagcc ttccga                                                   16

<210> SEQ ID NO 33
<211> LENGTH: 16
<212> TYPE: DNA
<213> ORGANISM: Artificial sequence
<220> FEATURE:
<223> OTHER INFORMATION: probe

<400> SEQUENCE: 33
aaatgaaacc ttccga                                                   16

<210> SEQ ID NO 34
```

```
<211> LENGTH: 15
<212> TYPE: DNA
<213> ORGANISM: Artificial sequence
<220> FEATURE:
<223> OTHER INFORMATION: probe

<400> SEQUENCE: 34
aagagaacgg agcag                                                      15

<210> SEQ ID NO 35
<211> LENGTH: 15
<212> TYPE: DNA
<213> ORGANISM: Artificial sequence
<220> FEATURE:
<223> OTHER INFORMATION: probe

<400> SEQUENCE: 35
aagagaatgg agcag                                                      15

<210> SEQ ID NO 36
<211> LENGTH: 15
<212> TYPE: DNA
<213> ORGANISM: Artificial sequence
<220> FEATURE:
<223> OTHER INFORMATION: probe

<400> SEQUENCE: 36
agagaacgga gcaga                                                      15

<210> SEQ ID NO 37
<211> LENGTH: 15
<212> TYPE: DNA
<213> ORGANISM: Artificial sequence
<220> FEATURE:
<223> OTHER INFORMATION: probe

<400> SEQUENCE: 37
agagaacaga gcaga                                                      15

<210> SEQ ID NO 38
<211> LENGTH: 15
<212> TYPE: DNA
<213> ORGANISM: Artificial sequence
<220> FEATURE:
<223> OTHER INFORMATION: probe

<400> SEQUENCE: 38
ggccacaaat ggcgt                                                      15

<210> SEQ ID NO 39
<211> LENGTH: 15
<212> TYPE: DNA
<213> ORGANISM: Artificial sequence
<220> FEATURE:
<223> OTHER INFORMATION: probe

<400> SEQUENCE: 39
ggccacaaac ggcgt                                                      15

<210> SEQ ID NO 40
<211> LENGTH: 15
<212> TYPE: DNA
<213> ORGANISM: Artificial sequence
<220> FEATURE:
<223> OTHER INFORMATION: probe

<400> SEQUENCE: 40
```

```
ggccacacac ggcgt                                                          15

<210> SEQ ID NO 41
<211> LENGTH: 15
<212> TYPE: DNA
<213> ORGANISM: Artificial sequence
<220> FEATURE:
<223> OTHER INFORMATION: probe

<400> SEQUENCE: 41
acaaatggcg tggtc                                                          15

<210> SEQ ID NO 42
<211> LENGTH: 15
<212> TYPE: DNA
<213> ORGANISM: Artificial sequence
<220> FEATURE:
<223> OTHER INFORMATION: probe

<400> SEQUENCE: 42
acaaatgatg tggtc                                                          15

<210> SEQ ID NO 43
<211> LENGTH: 15
<212> TYPE: DNA
<213> ORGANISM: Artificial sequence
<220> FEATURE:
<223> OTHER INFORMATION: probe

<400> SEQUENCE: 43
caaacggcgt ggtcc                                                          15

<210> SEQ ID NO 44
<211> LENGTH: 15
<212> TYPE: DNA
<213> ORGANISM: Artificial sequence
<220> FEATURE:
<223> OTHER INFORMATION: probe

<400> SEQUENCE: 44
caaacgatgt ggtcc                                                          15

<210> SEQ ID NO 45
<211> LENGTH: 15
<212> TYPE: DNA
<213> ORGANISM: Artificial sequence
<220> FEATURE:
<223> OTHER INFORMATION: probe

<400> SEQUENCE: 45
gtggtccatg tcatc                                                          15

<210> SEQ ID NO 46
<211> LENGTH: 15
<212> TYPE: DNA
<213> ORGANISM: Artificial sequence
<220> FEATURE:
<223> OTHER INFORMATION: probe

<400> SEQUENCE: 46
gtggtccgtg tcatc                                                          15
```

MULTI-SPOT METAL-CAPPED NANOSTRUCTURE ARRAY NUCLEIC ACID CHIP FOR DIAGNOSIS OF CORNEAL DYSTROPHY AND PREPARATION METHOD THEREOF

TECHNICAL FIELD

The present invention relates to a multi-spot metal-capped nanostructure array nucleic acid chip for diagnosing corneal dystrophy, and more particularly to a multi-spot metal-capped nanostructure array nucleic acid chip capable of employing LSPR (localized surface plasmon resonance) optical properties, a preparation method thereof, and a multi-spot metal-capped nanostructure array nucleic acid chip for diagnosing BIGH3 gene mutations, which can diagnose various corneal dystrophies.

BACKGROUND ART

Corneal dystrophy is an autosomal dominant inherited disease in which clouding occurs in the central cornea and increases with age to reduce sight. Corneal dystrophies include Avellino corneal dystrophy (ACD), lattice type I corneal dystrophy (LCD), and Reis-bucklers corneal dystrophy (RBCD), and are caused by a mutation in a gene that encodes BIGH3 protein. Patients with heterozygous Avellino corneal dystrophy experience significant sight loss with age, and patients with homozygous Avellino corneal dystrophy loss their sight from 6 years old age. Avellino corneal dystrophy was previously commonly called granular corneal dystrophy, but it was found to have a genetic difference and was newly named in 1988. Avellino corneal dystrophy is known as corneal dystrophy which is the most frequent worldwide, and the results of gene testing indicate that Avellino corneal dystrophy (heterozygous) is a significantly frequent disease with a prevalence rate of 1/340 to 1/1,000 in Korea (Holland, E. J. et al., *Ophthalmology*, 99:1564, 1992; Kennedy, S. M. et al., *Br. J. Ophthalmol.*, 80:489, 1996; Dolmetsch, A. M. et al., *Can. J. Ophthalmol.*, 31:29, 1996; Afshari, N. A. et al., *Arch. Ophthalmol.*, 119:16, 2001; Stewart, H. S. Hum. Mutat., 14:126, 1999).

It was found that, when patients with heterozygous Avellino corneal dystrophy receive Lasik eye surgery, corneal clouding starts to increase rapidly 2 years after the surgery, resulting in blindness (Jun, R M et al., *Ophthalmolgy*, 111: 463, 2004). Thus, before Lasik eye surgery is performed, accurate diagnosis for patients with Avellino corneal dystrophy should be performed in order to prevent symptoms caused by Lasik eye surgery from progressing. However, oculists have diagnosed Avellino corneal dystrophy by examining eye clouding with a microscope, and for this reason, in some cases, patients who did not develop symptoms of Avellino corneal dystrophy were not found and were subjected to Lasik eye surgery, thus losing their sight. Accordingly, there is an urgent need for an accurate and rapid method for diagnosing Avellino corneal dystrophy.

In order to rapidly diagnose a specific mutation in the BIGH3 gene to diagnose corneal dystrophies, including Avellino corneal dystrophy, the present inventors developed an oligonucleotide for detecting a mutation in the BIGH3 gene, and a nucleic acid chip for diagnosing corneal dystrophy, which has the oligonucleotide immobilized thereon (Korean Patent Laid-Open Publication No. 10-207-0076532). However, this type of nucleic acid chip has problems in that a labeling operation for detecting target DNA is complicated, the measurement time is long, and the measurement system is large-sized, which makes it difficult to perform a measurement in a simple and easy manner.

In an attempt to solve the problems of nucleic acid chips based on a labeling operation, a new type of label-free biochip based on localized surface plasmon resonance (LSPR), a new optical property that is expressed only in nanostructures, was fabricated. When materials having a local surface, such as metal nanoparticles, are radiated with light having various wavelengths, the surface of the metal nanoparticles is polarized, unlike a bulk metal, and the strength of the electric field is increased. Electrons formed by the polarization form a Plasmon and oscillate locally on the surface of the metal nanoparticles. This phenomenon is referred to as LSPR. The LSPR optical properties sensitively respond to a change in permittivity, that is, a change in refractive index, which occurs near nanoparticles, and thus make it possible to analyze biomolecular interactions with high sensitivity in a simply manner compared to label-free biosensors which use a quartz crystal microbalance (QCM) or electrochemical method. In addition, the LSPR optical properties show an absorption peak in the visible light region, and thus make it possible to analyze biomolecular interactions by an optical system which is simpler than label-free biosensors employing SPR optical properties, developed to date. Thus, a biochip, which is based on the LSPR optical properties as a detection principle and has various ligands immobilized on a single biochip, can simultaneously analyze multiple analytes, unlike conventional biochips, and thus enables on-site monitoring which is required in label-free biochips.

As the beginning of an LSPR sensor based on a gold nanoparticle array biochip, the Okamoto group of Japan's RIKEN immobilized gold nanoparticles on a glass substrate and reported the results of observing the change in LSPR properties with the change in refractive index of a liquid sample (T. Okamoto et. al., *Optics Letters*, 25:374, 2000). The Nath and Chilkoti group of Duke University, USA developed an LSPR biosensor based on a gold nanoparticle array biochip using the same technology (N. Nath and A. Chilkoti, *Anal. Chem.*, 74:509, 2002) and reported the results of observing the interaction between biomolecules in real time (N. Nath and A. Chilkoti, *Anal. Chem.*, 74:509, 2002). In addition, these observed the change in measurement sensitivity according to the size of gold nanoparticles, thereby succeeding in optimization of a metal nanoparticle array biochip. However, this type of LSPR biochip has problems in that a process of fabricating metal nanoparticles is complicated and time-consuming, it is difficult to fabricate metal nanoparticles having various sizes, and nanoparticles are irregularly immobilized, making it difficult to ensure reproducibility.

In an attempt to solve these problems, the E. Tamiya group of the Japanese JAIST and Osaka University have conducted studies on the development of an LSPR biosensor based on a metal nanoparticle array biochip of a new structure from 2004 and developed a metal-capped nanoparticle array biochip, which can exhibit the same effect as that of nanoparticles of various sizes arrayed on the substrate surface, by immobilizing silica nanoparticles of uniform size on a glass substrate and then depositing a metal on the surface of the arrayed nanoparticles to various thicknesses (Japanese Patent Laid-Open Publication No. P2006-250668A). In addition, the E. Tamiya group demonstrated that the nanoparticle array biochip can be applied as an LSPR optical property-based label-free optical sensor capable of detecting the interaction between biomolecules, including DNA, RNA, peptides and proteins. However, this type of LSPR-based biosensor still has problems in that the fabrication time is long and it is difficult to simultaneously measure multiple analyte biomolecules and to distinguish between the multiple biomolecules.

Accordingly, the present inventors have made extensive efforts to use the above-described various characteristics of the prior art and to solve the above-described problems occurring in the prior art and, as a result, have fabricated a multi-spot metal-capped nanostructure array nucleic acid chip for diagnosing corneal dystrophy, which can simultaneously detect multiple analyte DNAs by a single chip using LSPR optical properties, and have found that the multi-spot metal-capped nanostructure array nucleic acid chip for diagnosing corneal dystrophy can detect a plurality of target nucleic acids at a time, thereby completing the present invention.

DISCLOSURE OF INVENTION

It is an object of the present invention to provide a multi-spot metal-capped nanostructure array nucleic acid chip for diagnosing corneal dystrophy, which can simultaneously detect multiple analyte nucleic acids by a single chip using LSPR optical properties.

Another object of the present invention is to provide a multi-spot metal-capped nanostructure array nucleic acid chip for diagnosing corneal dystrophy, which can perform the multiple detections and quantification of DNAs having BIGH3 gene mutations for diagnosing corneal dystrophies, including Avellino corneal dystrophy, which should be accurately diagnosed before sight correction surgery using the nucleic acid chip.

To achieve the above object, the present invention provides a method for preparing a multi-spot metal-capped nanostructure array nucleic acid chip, the method comprising the steps of: (a) forming a metal thin film layer (second layer) on a substrate (first layer); (b) forming multi-spots on the metal thin film layer (second layer) and arraying nanostructures on the respective surfaces of the multi-spots at constant intervals to form a nanostructure layer (third layer); (c) forming a metal thin film layer (fourth layer) on the nanostructure layer; and (d) immobilizing a probe nucleic acid on the metal thin film (fourth layer).

The present invention provides a multi-spot metal-capped nanostructure array nucleic acid chip for diagnosing corneal dystrophy, which is prepared by the above-described method and comprises: (a) a substrate (first layer); (b) a metal thin film layer (second layer) formed on the substrate; (c) a nanostructure layer (third layer) comprising multi-spots, formed on the metal thin film layer, and nanostructures arrayed on the respective surfaces of the multi-spots at constant intervals; (d) a metal thin film layer (fourth layer) formed on the surface of the nanostructure layer; and (e) probe nucleic acids immobilized on the metal thin film (fourth layer).

The present invention also provides a method for detecting a target nucleic acid, the method comprising: allowing the target nucleic acid to react with said multi-spot metal-capped nanostructure array nucleic acid chip for diagnosing corneal dystrophy; and radiating light to the multi-spot metal-capped nanostructure array nucleic acid chip and analyzing a change in localized surface plasmon resonance (LSPR) of the nucleic acid chip.

The present invention also provides a multi-spot metal-capped nanostructure array nucleic acid chip for diagnosing corneal dystrophy, the nucleic acid chip comprising: (a) a substrate (first layer); (b) a metal thin film layer (second layer) formed on the substrate; (c) a nanostructure layer (third layer) comprising multi-spots, formed on the metal thin film layer, and nanostructures arrayed on the respective surfaces of the multi-spots at constant intervals; (d) a metal thin film layer (fourth layer) formed on the surface of the nanostructure layer; and (e) probe nucleic acids for detecting a BIGH3 gene mutation, immobilized on the metal thin film (fourth layer).

The present invention also provides a method for detecting a BIGH3 gene mutation, the method comprising: allowing a clinical sample to react with said multi-spot metal-capped nanostructure array nucleic acid chip for diagnosing corneal dystrophy; and radiating light to the multi-spot metal-capped nanostructure array nucleic acid chip and analyzing a change in localized surface plasmon resonance (LSPR) of the nucleic acid chip.

Other features and embodiments of the present invention will be more apparent from the following detailed descriptions and the appended claims

BRIEF DESCRIPTION OF THE DRAWINGS

FIG. 1 is a schematic view showing an example of a multi-spot metal-capped nanostructure array nucleic acid chip for diagnosing corneal dystrophy according to the present invention and is a set of photographs of multi-spot metal-capped nanostructure array nucleic acid chips.

BEST MODE FOR CARRYING OUT THE INVENTION

Figure 2:
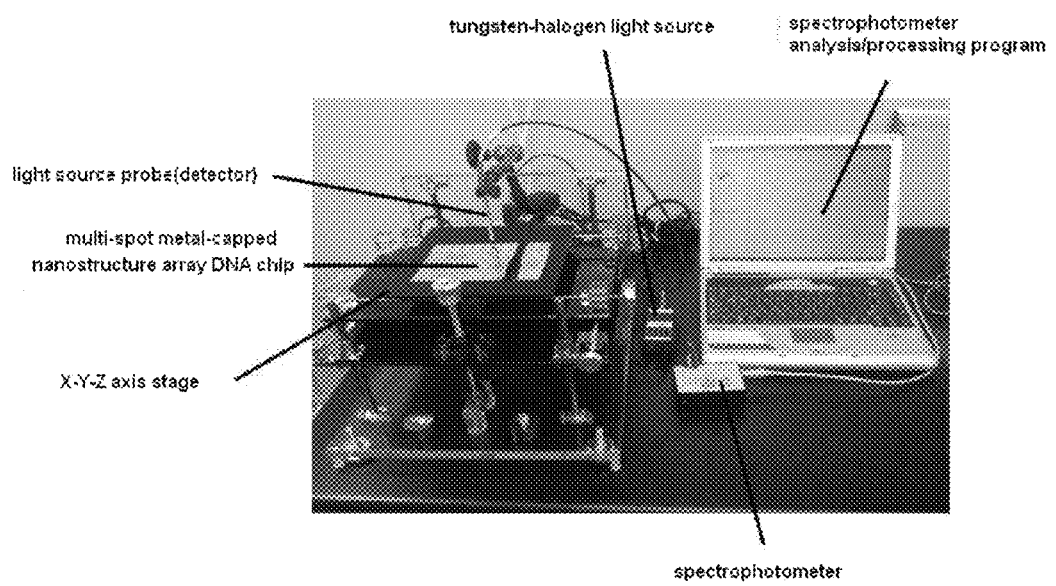
FIG. 2 is a photograph of an LSPR optical property-based label-free biosensor comprising a multi-spot metal-capped nanostructure array nucleic acid chip for diagnosing corneal dystrophy according to the present invention.

Unless defined otherwise, all technical and scientific terms used herein have the same meaning as commonly understood by one of ordinary skill in the art to which the invention pertains. Generally, the nomenclature used herein and the experiment methods are those well known and commonly employed in the art.

In one aspect, the present invention is directed to a for preparing a multi-spot metal-capped nanostructure array nucleic acid chip, the method comprising the steps of: (a) forming a metal thin film layer (second layer) on a substrate (first layer); (b) forming multi-spots on the metal thin film layer (second layer) and arraying nanostructures on the respective surfaces of the multi-spots at constant intervals to form a nanostructure layer (third layer); (c) forming a metal thin film layer (fourth layer) on the nanostructure layer; and (d) immobilizing a probe nucleic acid on the metal thin film (fourth layer). The present invention is also directed to a multi-spot metal-capped nanostructure array nucleic acid chip for diagnosing corneal dystrophy, which is prepared by the above-described method and comprises: (a) a substrate (first layer); (b) a metal thin film layer (second layer) formed on the substrate; (c) a nanostructure layer (third layer) comprising multi-spots, formed on the metal thin film layer, and nanostructures arrayed on the respective surfaces of the multi-spots at constant intervals; (d) a metal thin film layer (fourth layer) formed on the surface of the nanostructure layer; and (e) probe nucleic acids immobilized on the metal thin film (fourth layer).

In the present invention, the metal thin film (fourth layer) can be formed on the multi-spot type nanostructure layer (third layer) using a vacuum deposition system or the like, and the nanostructure layer (third layer) can be immobilized on the metal thin film (second layer) using, for example, a porous mask, such that multi-spots can be formed.

In the present invention, the nanostructure layer (third layer) may have a single structure, and the probe nucleic acid may consist of a plurality of probe DNAs that recognize a plurality of target DNAs.

In the present invention, the substrate may be made of a material selected from the group consisting of glass, polystyrene, polyethylene terephthalate (PET), polycarbonate, silicon, and quartz. The above-mentioned substrates does not show anisotropy for polarization and have excellent processability. Particularly, the glass, polystyrene, PET and polycarbonate substrates are transparent for white light. When the substrate surface has a color, incident white light will be reflected from the substrate surface and will influence optical properties such as LSPR properties. For this reason, it is preferable to use a transparent substrate having the property of transmitting incident white light without reflecting the incident white light.

In the present invention, the thickness of the substrate may be between 0.1 mm and 20 mm, which are the smallest thickness and largest thickness of substrates which have been constructed to date or can be introduced.

The metal thin film layers (second layer and fourth layer) for the multi-spot metal-capped nanostructure array nucleic acid chip according to the present invention are not specifically limited, so long as they can be obtained by generation of localized surface plasmon resonance. For example, these layers may be made of a metal selected from the group consisting of gold (Au), silver (Ag), copper (Cu), aluminum (Al), platinum (Pt), nickel (Ni), zinc (Zn), and mixtures thereof. Also, the wavelength region of absorption spectrum peaks occurring due to LSPR optical properties varies depending on the thickness of the metal thin film layer on the surface of the layer of nanostructures (third layer) which are arrayed at constant intervals. Thus, it is possible to fabricate a new type of multi-spot metal-capped nanostructure array nucleic acid chip which can react in various visible light regions.

The formation of the metal thin film layers (second layer and fourth layer) for the multi-spot metal-capped nanostructure nucleic acid chip according to the present invention can be performed by sputtering, vapor deposition, ion plating, electroplating, electroless plating, etc. The thicknesses of the metal thin film layers (second layer and fourth layer) can be optionally determined depending on the shape, size and array state of the nanostructures of the third layer. For example, in the case in which the nanostructures are 100-nm spherical particles, the second layer and the fourth layer are preferably formed to thicknesses of 30 nm to 50 nm and 20 nm to 40 nm, respectively.

"The layer of nanostructures arrayed at constant intervals" for the multi-spot metal-capped nanostructure nucleic acid chip according to the present invention means that nano-sized structures are arrayed at constant intervals. The nanostructures do not influence LSPR optical properties, and thus are not specifically limited. For example, the nanostructures may be selected from the group consisting of nano-particles, nano-dots, nano-islands, nano-rods, and nano-wires.

A porous mask may be used so that the nanostructure layer (third layer) for the multi-spot metal-capped nanostructure array nucleic acid chip of the present invention are formed in the form of multi-spots. The porous mask is attached to the metal thin film layer such that nanostructures are arrayed at constant intervals only in pores formed through the mask surface, and multi-spots are formed on the surface of the metal thin film layer (second layer). The porous mask that may be used in the present invention may be selected from the group consisting of a rubber flat plate, a silicon flat plate, and a mixture thereof. The porous mask is prepared by forming pores through the surface of the flat plate using a punching machine or the like.

In the present invention, the pore number of the porous mask may be between 1 and 150, which are the lowest value and highest value of the pore number of porous masks which have been constructed to date or can be introduced.

The array of the nanostructures of the third layer on the metal thin film layer (second layer) of the multi-spot metal-capped nanostructure array nucleic acid chip at constant intervals can be performed by forming a self-assembly monolayer (SAM) film having a carboxyl group on the surface of the metal thin film layer (second layer) using 4,4'-dithiodibutylic acid (DDA), immobilizing an amine group on the surface of the nanostructures using 3-aminopropyltriethoxy silan (γ-APTES), and then forming a covalent bond between the SAM film and the amine group.

When the surface of the multi-spot metal-capped nanostructure array nucleic acid chip is radiated with light, polarization will occur in the nucleic acid chip, and electrons formed by the polarization will form a plasmon and oscillate locally on the surface of the nucleic acid chip, thus generating LSPR optical properties.

Immobilization of one or more probe nucleic acids in the present invention can be performed using a nucleic acid immobilization method which is conventionally used to immobilize nucleic acids in the art. The probe nucleic acids are not limited, so long as they can bind specifically to target nucleic acids or candidate target nucleic acids in a sample and can be immobilized on a metal film. The immobilization of the probe nucleic acids on the multi-spot metal thin film layer (fourth layer) is preferably performed by physical adsorption or chemical bonding.

Probe nucleic acids for detection of genetic information, which are prokaryotic or eukaryotic or derived from prokaryotic or eukaryotic cells, should have specificity only for target nucleic acids to be detected. To construct such probe nucleic acids, a group of candidate probe nucleic acids for each target gene or organism is first selected.

The group of candidate probe nucleic acids is determined within the gene portion in which target nucleic acids are located. Whether the candidate probe nucleic acids have specificity was determined by comparing similarity between base sequences through BLAST searching, strains are applied in hybridization reactions, and probe nucleic acids that react only with the respective target genes are selected for identification in the candidate group. In addition, the above-selected probe nucleic acids for identification are applied to clinical tests for various biological samples to determine their sensitivity.

The probe nucleic acids selected according to the present invention are 13-17-mer oligonucleotides and preferably have a homology of 70%, 80%, 90%, 95% or higher with the complete complementary sequence of a target to be detected. The nucleic acid probe for detection and identification of each target according to the present invention may comprise 50 or more oligonucleotides.

The nucleotides that are used in the present invention may be ribonucleotides, deoxyribonucleotides, and modified nucleotides, such as nucleotides containing inosine or modified bases, but these should not influence hybridization characteristics.

In another aspect, the present invention is also directed to a multi-diagnosis method comprising the steps of: allowing the multi-spot metal-capped nanostructure array nucleic acid chip for diagnosing corneal dystrophy, which has the probe nucleic acids immobilized thereon, to contact with a target nucleic acid comprising a plurality of nucleic acids having BIGH3 gene mutations, and performing multiple detections and/or quantitative analysis of the nucleic acids.

As used herein, the term "target nucleic acid" refers to a nucleic acid that can bind specifically to a probe nucleic acid. The candidate target nucleic acids are nucleic acids that can be predicted to bind specifically to probe nucleic acids, and specific candidate target nucleic acids are the same as target nucleic acids. A sample refers to a solution containing a target nucleic acid or a candidate target nucleic acid. Examples of the sample include, but are not limited to, blood, salvia, urine, nosebleed, tears, excretions, tissue extracts, culture broths, and the like.

In order to provide a nucleic acid substrate for use in the diagnosis of disease in the biological sample of the present invention, a target nucleic acid is extracted from the sample. DNA can be extracted from various samples using standard techniques or commercially available kits. For example, kits that are used to isolate RNA or DNA from tissue samples can be purchased from Qiagen, Inc. (USA) and Stratagene (USA). A QIAAMP blood kit enables the isolation of DNA from blood, marrow, body fluids or cell suspensions. A QIAAMP tissue kit enables the isolation of DNA from muscles and organs. If a target nucleic acid is a double-strand chain, denaturation is preferably performed before a detection process is carried out. Denaturation of single-strand DNA can be performed by a known method for chemical, physical or enzymatic denaturation. Particularly, it can be performed by heating to suitable temperature, preferably 80° C. or higher.

Also, a target nucleic acid that hybridizes with a probe nucleic acid can usually be prepared by two methods. The first method is a method that is used in Southern blot or Northern blot, in which genomic DNA or plasmid DNA is digested with a suitable restriction enzyme and then electrophoresed on agarose gel to separate DNA fragments according to size. The second method is a method of amplifying a desired DNA portion by PCR.

Examples of the PCR method that may be used in the present invention include the most common PCR method of performing amplification using the same amount of forward and reverse primers, an asymmetric PCR method capable of simultaneously obtaining a double-strand band and a single-strand band by asymmetrically adding forward and reverse primers, a multiplex PCR method capable of performing amplification using various primer pairs at a time, a ligase chain reaction (LCR) method of performing amplification using specific primers and ligase and then determining fluorescence by an enzyme immunoassay, as well as hot-start PCR, nest-PCR, modified oligonucleotide primer PCR, reverse transcriptase PCR, semi-quantitative reverse transcriptase PCR, real-time PCR, SACE (rapid amplification of cDNA ends), competitive PCR, short tandem repeats (STR), single-strand conformation polymorphism (SSCP), in situ PCR, DDRT-PCR (differential display reverse transcriptase PCR) and the like.

In a preferred embodiment of the present invention, asymmetric PCR is performed using DNA of an isolated analyte as a template, thereby constructing a fragment gene. The fragment gene is obtained using one-step PCR by adding a forward primer and a reverse primer at a ratio of 1:5.

In a preferred embodiment of the present invention, a PCR reaction is performed using a PCR mix containing 5 µl of 10×PCR buffer (100 mM Tris-HCl (pH 8.3), 500 mM KCl, 15 mM $MgCl_2$), 4 µl of dNTP mixture (2.5 mM of each of dATP, dGTP, dCTP and dTTP), 0.5 µl of 10 pmole forward primer, 2.5 µl of 10 pmole reverse primer, 1 µl of a 1/10 dilution of template DNA (100 ng), 0.5 µl of Taq polymerase (5 units/µl, Takara Shuzo Co., Shiga, Japan) and water making a total volume of 50 µl, under the following conditions: 10 cycles of initial denaturation at 94° C. for 7 min; then second denaturation at 94° C. for 1 min, annealing at 52° C. for 1 min and extension at 72° C. for 1 min; followed by 30 cycles of denaturation at 94° C. for 1 min, annealing at 54° C. for 1 min and extension at 72° C. for 1 min; and final extension at 72° C. for 5 min. The PCR reaction product is confirmed by agarose gel electrophoresis.

In another aspect, the present invention is directed to a method for detecting a target nucleic acid, the method comprising: allowing the target nucleic acid to react with the above-described multi-spot metal-capped nanostructure array nucleic acid chip for diagnosing corneal dystrophy; and radiating light to the multi-spot metal-capped nanostructure array nucleic acid chip and analyzing a change in localized surface plasmon resonance (LSPR) of the nucleic acid chip.

The multi-spot metal-capped nanostructure array nucleic acid chip of the present invention can be combined with analysis devices, including a light source, a detector, a spectrophotometer and an analysis device such as a computer, to provide an LSPR optical property-based label-free optical biosensor which can perform the multiple detections and quantification of nucleic acids attached to the chip surface.

In still another aspect, the present invention is directed to a multi-spot metal-capped nanostructure array nucleic acid chip for diagnosing corneal dystrophy, the nucleic acid chip comprising: (a) a substrate (first layer); (b) a metal thin film layer (second layer) formed on the substrate; (c) a nanostructure layer (third layer) comprising multi-spots, formed on the metal thin film layer, and nanostructures arrayed on the respective surfaces of the multi-spots at constant intervals; (d) a metal thin film layer (fourth layer) formed on the surface of the nanostructure layer; and (e) probe nucleic acids for detecting a BIGH3 gene mutation, immobilized on the metal thin film (fourth layer).

In the present invention, the probe nucleic acids for detecting a BIGH3 gene mutation may necessarily contain one or more base sequences selected from the group consisting of SEQ ID NO: 11 to SEQ ID NO: 46.

In the present invention, SEQ ID NOS: 11 to 46 are probe nucleic acids which can confirm mutations of mutation spots, which cause Avellino corneal dystrophy (ACD), lattice type I corneal dystrophy (LCD) and Reis-bucklers corneal dystrophy (RBCD), among BIGH3 gene mutation hot spots causing ocular diseases.

In yet another aspect, the present invention is directed to a method for detecting a BIGH3 gene mutation, the method comprising: allowing a clinical sample to react with said multi-spot metal-capped nanostructure array nucleic acid chip for diagnosing corneal dystrophy of claim 16; and radiating light to the multi-spot metal-capped nanostructure array nucleic acid chip and analyzing a change in localized surface plasmon resonance (LSPR) of the nucleic acid chip.

In the present invention, examples of the clinical samples may include, but are not limited to, blood, salvia, urine, nosebleed, tears, excretions, tissue extracts, culture broths, and the like.

The use of the inventive multi-spot metal-capped nanostructure array nucleic acid chip for diagnosing a BIGH3 gene mutation enables the selective detection of complementary target nucleic acids and mismatch target nucleic acids for all the target nucleic acids of homozygous and heterozygous corneal dystrophies.

EXAMPLES

Hereinafter, the present invention will be described in further detail with reference to examples. It will be obvious to a person having ordinary skill in the art that these examples are illustrative purposes only and are not to be construed to limit the scope of the present invention.

All the experiments in the following examples were conducted under the approval of the IRB committee of Yonsei Severance Hospital after obtaining informed consent from all volunteers in accordance with the Declaration of Helsinki.

Example 1

Preparation of Multi-Spot Metal-Capped Nanostructure Array Nucleic Acid Chip for Diagnosing Corneal Dystrophy Each of chromium and gold was vacuum-deposited on the surface of a slide glass substrate (first layer; 75 mm×25 mm×1 mm) using a vacuum deposition system (Shinu MST Co.,
Ltd., Korea), thereby forming a gold thin film layer (second layer). Specifically, chromium as the intermediate metal thin film was deposited to a thickness of 5 nm, and the thickness of the gold thin film layer could be controlled to 40 nm. Then, a porous mask (15, 20, 60 or 140 spots) was fixed to the gold thin film layer (second layer) by adsorption. Then, on the surface of the gold thin film layer (second layer) having the porous mask adsorbed thereon, an SAM film was formed using 1 mM 4,4'-dithiodibutylic acid (DDA). Then, 400 mM EDC was added to the surface of the gold thin film layer (second layer), and activation of the carboxyl group introduced onto the surface was performed, after which 100-nm-diameter silica nanostructures surface-modified with 3-aminopropyltriethoxysilane (γ-APTES) were arrayed on the surface of the gold thin film layer (second layer) by covalent bonding. Then, on the surface of the nanostructure layer (third layer) consisting of the array of the 100-nm-diameter silica nanostructures, gold was vacuum-deposited to a thickness of 30 nm, thereby preparing multi-spot metal-capped nanostructure array nucleic acid chips for diagnosing corneal dystrophy having various spot numbers (FIG. 1).

Example 2

Construction of LSPR Optical Property-Based Label-Free Optical Biosensor Comprising Multi-Spot Metal-Capped Nanostructure Array Nucleic Chip for Diagnosing Corneal Dystrophy FIG. 2 shows a photograph of an LSPR optical property-based label-free optical biosensor comprising the multi-spot metal-capped nanostructure array nucleic acid chip for diagnosing corneal dystrophy prepared as described above. The LSPR optical property-based label-free optical biosensor comprising the multi-spot metal-capped nanostructure array nucleic chip for diagnosing corneal dystrophy comprises a tungsten-halogen light source (wavelength: 360 nm-2000 nm, Ocean Optics, Inc., USA), a detector (wavelength: 300 nm-1100 nm, Ocean Optics, Inc., USA), a spectrophotometer (wavelength: 200 nm-1100 nm, Ocean Optics, Inc., USA) for splitting the light detected by the detector, and an analysis/processing program (Ocean Optics, Inc., USA) for processing the results obtained in the spectrophotometer. Herein, the tungsten-halogen light source and the detector are included in one light source probe. Incident light emitted from the tungsten-halogen light source of the LSPR optical property-based label-free optical biosensor was allowed to be incident vertically onto the surface of the multi-spot metal-capped nanostructure array nucleic acid chip, and then the reflected light was detected by the detector, split by the spectrophotometer and analyzed by the analysis/processing program, thereby measuring the absorption spectrum of the multi-spot metal-capped nanostructure array nucleic acid chip for diagnosing corneal dystrophy.

Example 3

Determination of BIGH3 Gene Mutation Type

In order to construct a probe for diagnosing a mutation in the BIGH3 gene (National Center for Biotechnology Information, NCBI accession no. NM_000358) responsible for ocular diseases, including Avellino corneal dystrophy, BIGH3 gene mutation sites to be used for the construction of the probe were determined. The DNA base sequences and amino acid sequences of the BIGH3 gene mutation sites were analyzed and secured through the NCBI gene-related data-base GenBank and OMIM (Online Mendelian Inheritance in Man), and information on each allele was also secured. To test the effectiveness of the diagnosis chip, mutation types to be searched were first determined. Among BIGH3 gene hot spots, mutation spots causing Avellino corneal dystrophy (ACD), lattice type I corneal dystrophy (LCD) and Reis-bucklers corneal dystrophy (RBCD) were selected (Table 1). mutation region of the exon 4 region

TABLE 1

Ocular diseases for BIGH3 gene mutations

| Phenotyes | Amino acid mutations | Mutation sequences | Exon mutation regions | References |
|---|---|---|---|---|
| Avellino dystrophy | R124H | CGC → CAC | 4 | Invest Ophth Vis Sci 43: 949, 2002 |
| Lattice dystrophy | R124C | CGC → TGC | 4 | Invest Ophth Vis Sci 43: 949, 2002 |
| Reis-Bucklers (CDB1) | R124L | CGC → CTC | 4 | Invest Ophth Vis Sci 43: 949, 2002 |
| Reis-Bucklers I | R124S | CGC → AGC | 4 | Invest Ophth Vis Sci 43: 949, 2002 |
| Reis-Bucklers I | D123H | GAC → CAC | 4 | Invest Ophth Vis Sci 43: 949, 2002 |
| Reis-Bucklers I | V113I | GTT → ATT | 4 | Exp Eye Res 89: 172, 2009 |
| Reis-Bucklers I | R129R | AGG → AGA | 4 | Ophthamol 111: 1108, 2004 |
| Reis-Bucklers I | L217L | CTC → CTG | 6 | Cornea 28: 97, 2009 |
| Reis-Bucklers I | L269F | CTT → TTT | 7 | Invest Ophth Vis Sci 46: 121, 2005 |
| Reis-Bucklers I | N272N | AAC → AAT | 7 | Invest Ophth Vis Sci 46: 121, 2005 |
| Reis-Bucklers I | V327V | GTA → GTG | 8 | Cornea 28: 97, 2009 |
| Reis-Bucklers I | H310H | CAC → CAT | 8 | J Genet 85: 73, 2006 |
| Lattice dystrophy | P501T | CCA → ACA | 11 | Am J Hum Genet 62: 719, 1998 |
| Lattice dystrophy | L518R | CTG → CCG | 11 | Invest Ophth Vis Sci 43: 949, 2002 |
| Lattice dystrophy | L472L | CTC → CTT | 11 | J Genet 85: 73, 2006 |
| Lattice type IIIA | V505D | GTC → GAC | 11 | Jpn J Ophthalmol 49: 84, 2005 |
| Lattice type IIIA | A480V | GCG → GTG | 11 | J Hum Genet 43: 214, 1998 |
| Lattice type IIIA | M502V | ATG → GTG | 11 | Exp Eye Res 89: 172, 2009 |
| Lattice dystrophy | F540F | TTT → TTC | 11 | Cornea 28: 97, 2009 |
| Granular dystrophy | R555W | CGG → TGG | 12 | Invest Ophth Vis Sci 43: 949, 2002 |
| Lattice dystrophy | L518P | CTG → CCG | 12 | Nippon Ganka Gakkai Zasshi. 106: 352, 2002 |
| Lattice dystrophy | L527R | CTG → CGG | 12 | Br J Ophthalmol 89: 771, 2005 |
| Lattice dystrophy | N544S | AAT → AGT | 12 | Am J Ophthalmol 130: 516, 2000 |
| Lattice type IIIA | A546T | GCC → ACC | 12 | Am J Ophthalmol 129: 248, 2000 |
| Reis-Bucklers | F540 deletion | TTT → — | 12 | Invest Ophth Vis Sci 43: 949, 2002 |
| Reis-Bucklers II (CDB2) | R555Q | CGG → CAG | 12 | Invest Ophth Vis Sci 43: 949, 2002 |
| Lattice dystrophy | T538P | ACA → CCA | 12 | J Genet 85: 73, 2006 |
| Lattice dystrophy | F547S | TTC → TCC | 12 | Mol Vis 13: 1976, 2007 |
| Lattice dystrophy | V539D | GTC → GAC | 12 | Invest Ophth Vis Sci 46: 121, 2005 |
| Lattice dystrophy | F540S | TTT → TTC | 12 | Invest Ophth Vis Sci 46: 1133, 2005 |
| Lattice dystrophy | T538R | ACA → AGA | 12 | Invest Ophth Vis Sci 43: 949, 2002 |
| Lattice dystrophy | ΔF540 | 1665-1667 | 12 | Invest Ophth Vis Sci 43: 949, 2002 |
| Lattice type I | T538P | ACA → CCA | 12 | J Genet 85: 73, 2006 |

TABLE 1-continued

Ocular diseases for BIGH3 gene mutations

| Phenotyes | Amino acid mutations | Mutation sequences | Exon mutation regions | References |
|---|---|---|---|---|
| Lattice dystrophy | A546D | GCC → GAC | 12 | Mol Vis 13: 1695, 2007 |
| Lattice dystrophy | T528T | ACG → ACT | 12 | Invest Ophth Vis Sci 46: 1133, 2005 |
| Lattice dystrophy | L558P | CTC → CCC | 12 | Ophthalmol 223: 207, 2009 |
| Lattice dystrophy | N544S | AAT → AGT | 12 | Mol Vis 15: 974, 2009 |
| Lattice dystrophy | P551Q | CCA → CAA | 12 | Am J Ophthalmol 138: 772, 2004 |
| Lattice dystrophy | L558P | CTC → CCC | 12 | Ophthalmol 223: 207, 2009 |
| Lattice dystrophy | L550P | CTG → CCG | 12 | Exp Eye Res 89: 172, 2009 |
| Lattice dystrophy | G594V | GGT → GTT | 13 | Invest Ophth Vis Sci 46: 1133, 2005 |
| Lattice dystrophy | His572 deletion | CAC → del | 13 | Mol Vis 12: 142, 2006 |
| Lattice dystrophy | L569R | CTG → CGG | 13 | Am J Ophthalmol 136: 872, 2003 |
| Lattice dystrophy | H572R | TAC → TGC | 13 | Jpn J Ophthalmol 50: 403, 2006 |
| Lattice dystrophy | L509P | CTG → CCG | 13 | Br J Ophthalmol 93: 932, 2009 |
| Lattice dystrophy | H626R | CAT → CGT | 14 | Arch Soc Esp Oftalmol 81: 369, 2006 |
| Lattice dystrophy | N622H | AAC → CAC | 14 | Ophthalmol 106: 964, 1999 |
| Reis-Bucklers | G623D | GGC → GAT | 14 | Invest Ophth Vis Sci 43: 949, 2002 |
| Granular dystrophy | M619V | ATG → GTG | 14 | Arch Ophthalmol 126: 371, 2008 |
| Lattice dystrophy | V624M | GTG → ATG | 14 | Mol Vis 14: 495, 2008 |
| Lattice dystrophy | V624, V625 deletion | gtg gtc deletion | 14 | Invest Ophth Vis Sci 46: 1133, 2005 |
| Lattice type I | N622K | AAT → AAG | 14 | Invest Ophth Vis Sci 43: 949, 2002 |
| Lattice type IIIA | N622K | AAT → AAA | 14 | Invest Ophth Vis Sci 43: 949, 2002 |
| Lattice type IIIA | V626Sx | ΔG1926 → frame shift | 14 | Invest Ophth Vis Sci 43: 949, 2002 |
| Lattice type I/IIIA | G623D | GGC → GAC | 14 | Mol Vis 14: 1298, 2008 |

Example 4

Acquisition of Search Regions by Polymerase Chain Reaction (PCR)

In order to search all the mutations shown in Table 1 above, 5 pairs of PCR primers including exon 4, exon 11, exon and exon 14 regions were constructed. To amplify the mutation region of the exon 4 region, two pairs of primers were used. Among them, one pair of primers (primer 1 and primer 2) were primers determined to be suitable for a diagnostic DNA chip experiment, and the other pair of primers (primer 3 and primer 4) were constructed for direct base sequencing. Herein, a fluorescent substance was conjugated to the hydroxyl residue at the 5' end of the primer strand (reverse primer) complementary to a DNA probe to be searched. To confirm an effective primer pair on the chip, primer 2 was conjugated with Cy5, and primer 4 was conjugated with Cy3. Asymmetric PCR was performed using about 10-100 ng of DNA (collected from blood) as a template based on a total reaction volume of 50 μl, thereby constructing a fragment gene. The fragment gene was obtained using one-step PCR by adding the forward primer and the reverse primer at a ratio of 1:5 to 1:10. The PCR reaction was performed under the following conditions: 35 cycles of initial denaturation at 98° C. for 5 min; then second denaturation at 94° C. for 1 min, annealing at 55° C. for 1 min and extension at 72° C. for 1 min; followed by final extension at 72° C. for 7 min.

TABLE 2

Primers for amplifying regions including mutation

| Primers # | SEQ ID NOs: | Base sequences (5'→ 3') |
|---|---|---|
| 1 | 1 | agc cct acc act ctc aa |
| 2 | 2 | cag gcc tcg ttg cta ggg |
| 3 | 3 | ccc cag agg cca tcc ctc ct |

TABLE 2-continued

Primers for amplifying regions including mutation

| Primers # | SEQ ID NOs: | Base sequences (5'→ 3') |
|---|---|---|
| 4 | 4 | ccg ggc aga cgg agg tca tc |
| 5 | 5 | ctc gtg gga gta taa cca gt |
| 6 | 6 | tgg gca gaa gct cca ccc gg |
| 7 | 7 | cat tcc agt ggc ctg gac tct act atc |
| 8 | 8 | ggg gcc ctg agg gat cac tac tt |
| 9 | 9 | ctg ttc agt aaa cac ttg ct |
| 10 | 10 | ctc tcc acc aac tgc cac at |

Example 5

Preparation of Probe DNA for Diagnosing BIGH3 Gene Mutation

In order to search the mutations responsible for corneal dystrophies shown in Table 1, probes were constructed such that 5-8 base sequences, most preferably 7 base sequences, were placed at both sides of the mutated base sequence. A probe for normal persons was constructed such that the non-mutated normal base sequence was placed at the center of the constructed base sequence.

TABLE 3

Probe DNAs constructed for diagnosis of mutations responsible for ocular diseases

| SEQ ID NOs: | Genotypes | Normal or mutation | Probe sequences | Exon regions |
|---|---|---|---|---|
| 11 | Normal | R124 | acg gac cgc acg gag | 4 |
| 12 | Avellino dystrophy | R124H | acg gac cac acg gag | 4 |
| 13 | Reis-Bucklers(CDB1) | R124L | acg gac ctc acg gag | 4 |
| 14 | Normal | R124 | cac gga ccg cac gga | 4 |
| 15 | Lattice type I | R124C | cac gga ctg cac gga | 4 |
| 16 | Normal | P501 | gac ccc cc aat ggg | 11 |
| 17 | Lattice type IIIA | P501T | gac ccc cac aat ggg | 11 |
| 18 | Normal | L518 | agc atg ctg gta gct | 12 |
| 19 | Lattice dystrophy Pro | L518P | agc atg ccg gta gct | 12 |
| 20 | Normal | L527 | gca gga ctg acg gag | 12 |
| 21 | Lattice dystrophy Arg | L527R | gca gga cgg acg gag | 12 |
| 22 | Normal | F540 | aca gtc ttt gct ccc | 12 |
| 23 | Reis-Bucklers | F540 delection | ac aca gtc gct ccc ac | 12 |
| 24 | Normal | N544 | ccc aca aat gaa gcc | 12 |
| 25 | Lattice dystrophy ser1 | N544S | ccc aca agt gaa gcc | 12 |
| 26 | Normal | N544 | ccc aca aac gaa gcc | 12 |
| 27 | Lattice dystrophy ser2 | N544S | ccc aca agc gaa gcc | 12 |
| 28 | Lattice dystrophy ser3 | N544S | ccc aca tct gaa gcc | 12 |

TABLE 3-continued

Probe DNAs constructed for diagnosis of mutations responsible for ocular diseases

| SEQ ID NOs: | Genotypes | Normal or mutation | Probe sequences | Exon regions |
|---|---|---|---|---|
| 29 | Lattice dystrophy ser4 | N544S | ccc aca tcc gaa gcc | 12 |
| 30 | Lattice dystrophy ser5 | N544S | ccc aca tca gaa gcc | 12 |
| 31 | Lattice dystrophy ser6 | N544S | ccc aca tcg gaa gcc | 12 |
| 32 | Normal | A546 | aaa tga agc cttc cga | 12 |
| 33 | Lattice type IIIA thr | A546T | aaa tga aac cttc cga | 12 |
| 34 | Normal | R555 | aag aga acg gag cag | 12 |
| 35 | Granular dystrophy | R555W | aag aga atg gag cag | 12 |
| 36 | Normal | R555 | aga gaa cgg agc aga | 12 |
| 37 | Reis-Bucklers(CDB2) | R555Q | aga gaa cag agc aga | 12 |
| 38 | Normal | N622 | ggc cac aaa tgg cgt | 14 |
| 39 | Normal | N622 | ggc cac aaa cgg cgt | 14 |
| 40 | Lattice dystrophy his | N622H | ggc cac aca cgg cgt | 14 |
| 41 | Normal | G623 | aca aat ggc gtg gtc | 14 |
| 42 | Reis-Bucklers-1 | G623D | aca aat gat gtg gtc | 14 |
| 43 | Normal | G623 | caa acg gcg tgg tcc | 14 |
| 44 | Reis-Bucklers-2 | G623D | caa acg atg tgg tcc | 14 |
| 45 | Normal | H626 | gtg gtc cat gtc atc | 14 |
| 46 | 14 Lattice dystrophy | H626R | gtg gtc cgt gtc atc | 14 |

Example 6

Immobilization of Probe DNA on Surface of Multi-Spot Metal-Capped Nanostructure Array Nucleic Acid Chip for Diagnosing Corneal Dystrophy In order to apply each of the probe DNAs, selected in Example 5, to a nucleic acid chip, synthesis of the probe DNAs was performed. Specifically, a mononucletide (Proligo Biochemie GmbH Hamburg Co.) was introduced into an automatic synthesizer (Expedite™ 8900, PE Biosystems Co.), and the base sequence and scale of the desired probe DNA were input, thereby obtaining 0.05 pmole of each of pure nucleic acid probe DNAs. The obtained probe DNA was electrophoresed to confirm whether it was synthesized.

Figure 3:
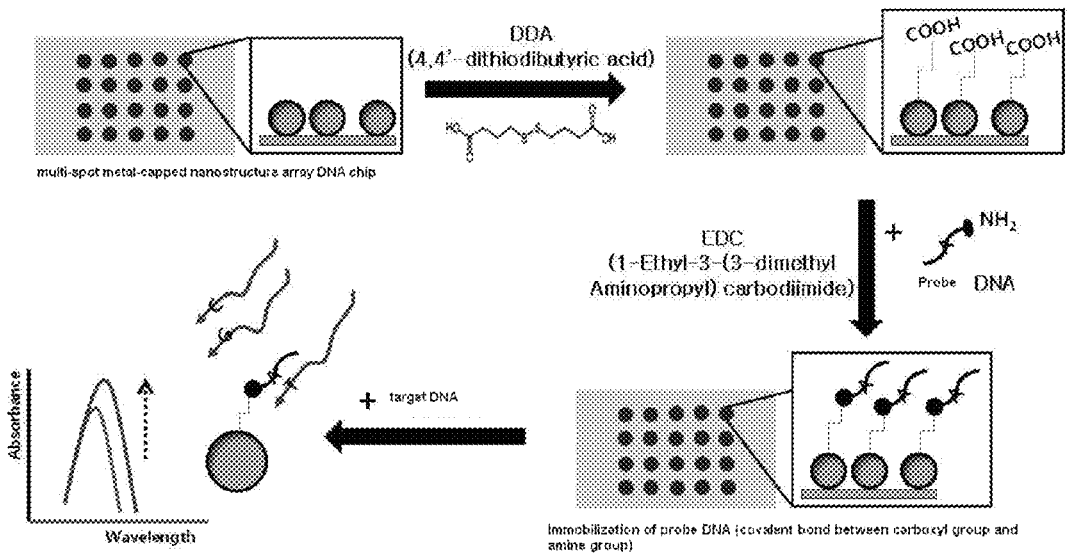
FIG. 3 is a schematic view showing a method of immobilizing a probe DNA on a multi-spot metal-capped nanostructure array nucleic acid chip for diagnosing corneal dystrophy according to the present invention and a process of inducing complementary binding by allowing a target DNA to react with the probe DNA.

FIG. 3 is a schematic view showing a method of immobilizing the above-designed probe DNA on the surface of the multi-spot metal-capped nanostructure array nucleic acid chip and a process of inducing complementary binding by allowing a target DNA to react with the probe DNA.

To immobilize the above-prepared probe DNA on the surface of the multi-spot metal-capped nanostructure array nucleic acid chip, a bond between a carboxyl group and an amine group was used. When all the DNA probe fragment probes were synthesized in order to immobilize the DNA probes, a base having an amino residue was inserted into the 3'-end of each of the probes using an aminolinker column (Cruachem, Glasgrow, Scotland). Also, on the surface of the multi-spot metal-capped nanostructure array nucleic acid chip for diagnosing corneal dystrophy, an SAM film having a carboxyl group was formed using 1 mM 4,4'-dithiodibutylic acid (DDA). Then, 400 mM EDC was added to the surface of the multi-spot metal-capped nanostructure array nucleic acid chip, and activation of the carboxyl group introduced onto the surface was performed, after which carboxyl-amine bonding was performed at a humidity of 55% or higher for 1 hour or more, thereby immobilizing the probe DNAs. Herein, each of the probe DNAs was immobilized at a concentration of 10-100 μM.

Example 7

Examination of Functionality of Nucleic Acid Chip as a Function of Length of Target DNA Using the LSPR optical property-based label-free optical biosensor comprising the multi-spot metal-capped nanostructure array nucleic acid chip constructed in Example 2, the detection efficiency of the nucleic acid chip as a function of the length of each of normal target DNA and the target DNAs of Avellino corneal dystrophy (ACD), lattice type I corneal dystrophy (LCD) and Reis-bucklers corneal dystrophy (RBCD) was measured. Each the probe DNAs having a length of 15 mer was immobilized on the surface of the nucleic acid chip, and each of the target DNAs having lengths of 30, 50, 100, 147, 190 and 225 mer was allowed to react with the probe DNA at a humidity of 55% or higher for 6 hours or more, thereby inducing complementary binding therebetween. The 30-mer target DNA was obtained by synthesis, and other target DNAs were obtained by PCR reaction.

Figure 4:
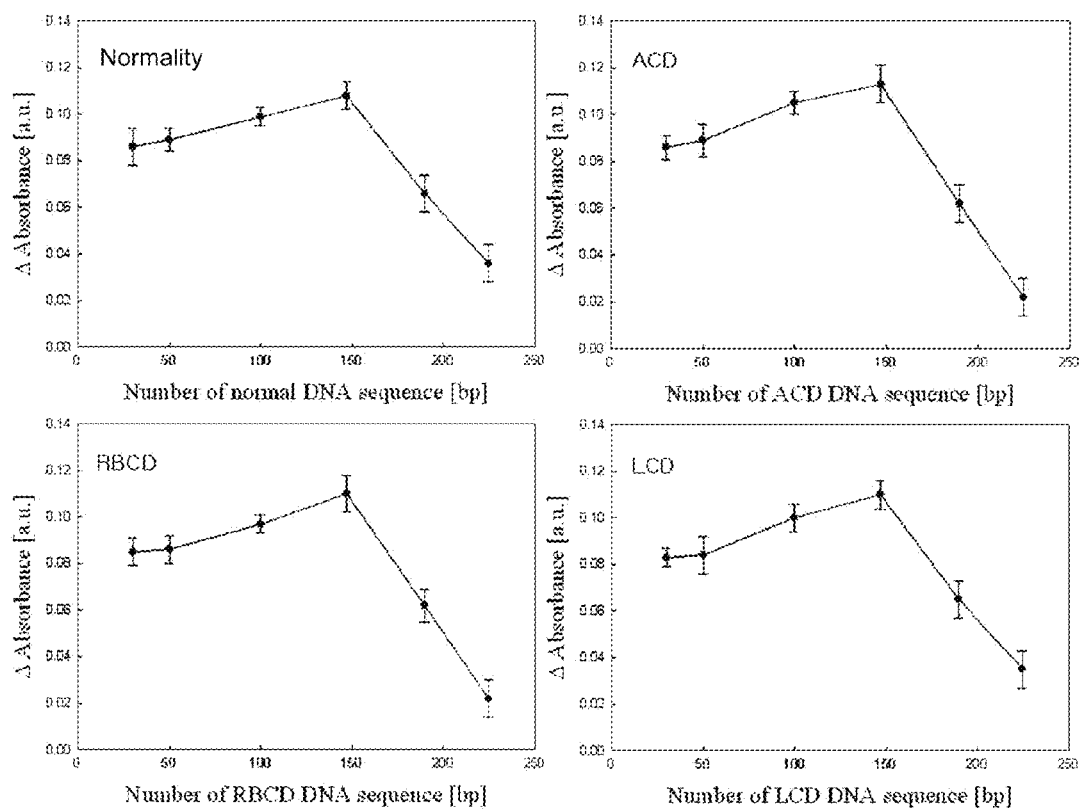
FIG. 4 shows the results of measuring the detection efficiency of a nucleic acid chip as a function of the length of each of normal target DNA and the target DNAs of Avellino corneal dystrophy (ACD), Reis-bucklers corneal dystrophy (RBCD) and lattice type I corneal dystrophy (LCD) using an LSPR optical property-based label-free optical biosensor comprising a multi-spot metal-capped nanostructure array nucleic acid chip for diagnosing corneal dystrophy according to the present invention.
Figure 5:
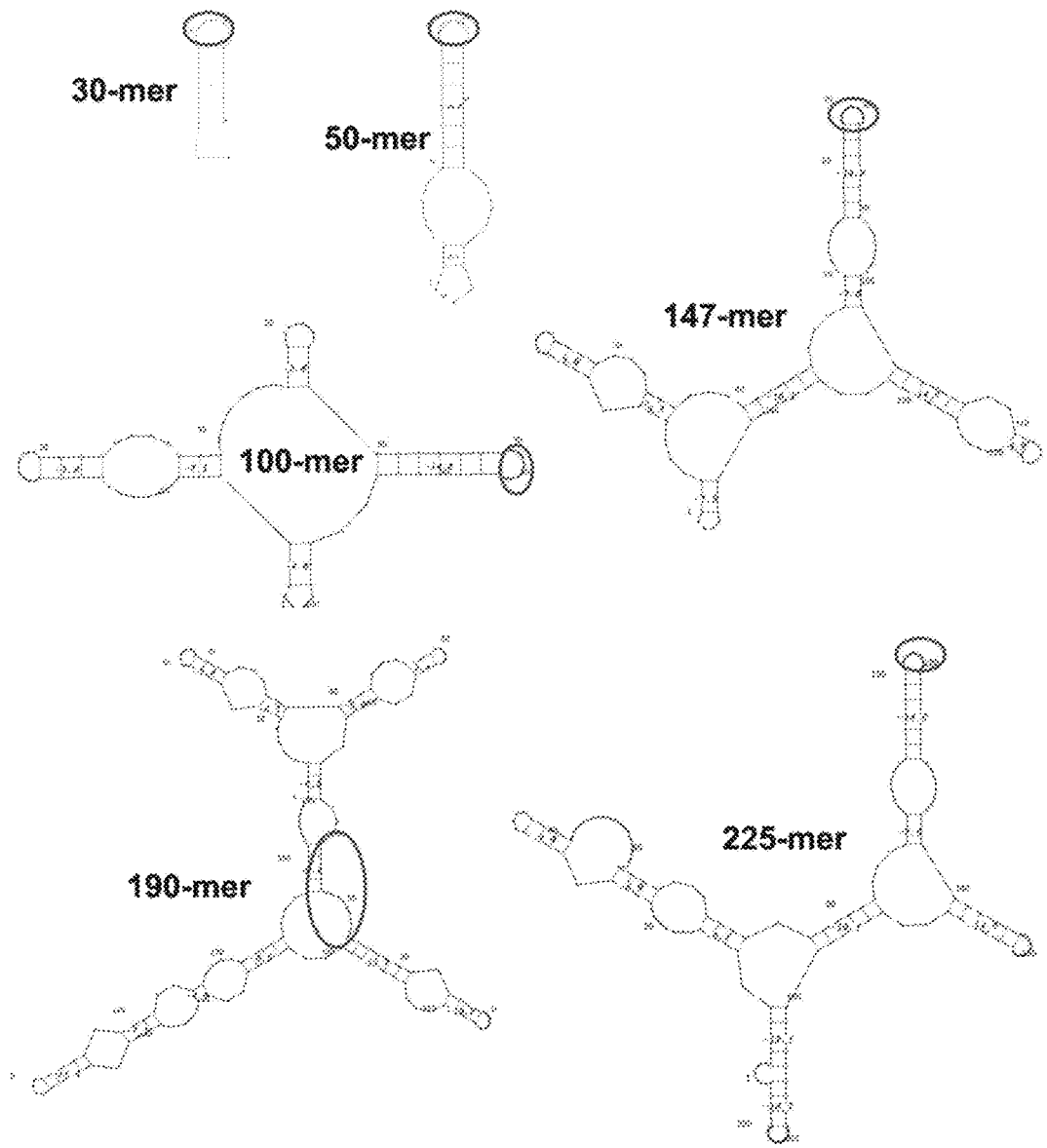
FIG. 5 shows the results of a simulation test performed to predict the secondary structure according to the length of each target DNA, which binds to a probe DNA, using the prediction program (GeneBee). The secondary structure predicted as a function of the length of the target DNA was obtained by the Greedy method, and the red oval portion shown in the secondary structure predicted as a function of the length of each target DNA indicates the binding site of the target DNA, which can complementarily bind to the binding site of the probe DNA.

As a result, as shown in FIG. 4, the target DNAs showed the highest efficiency at a length of 147 mer. FIG. 5 shows the results of performing a simulation test with a prediction program (GeneBee; http://www.genebee.msu.su/services/rna2_reduced.html) to predict the secondary structure according to the length of each target DNA binding to the probe DNA. The secondary structure according to the length of the target DNA was obtained by the Greedy method. As a result, as can be seen in FIG. 5, when the target DNA had a length of 147 mer or less, the binding site (red oval portion) of the target DNA could bind complementarily to the binding site of the probe DNA, but when the target DNA had a length of 190 mer or more, the complementary binding thereof was difficult. Thus, a subsequent experiment was performed using each target DNA having a length of 147 mer.

Example 8

Figure 6:
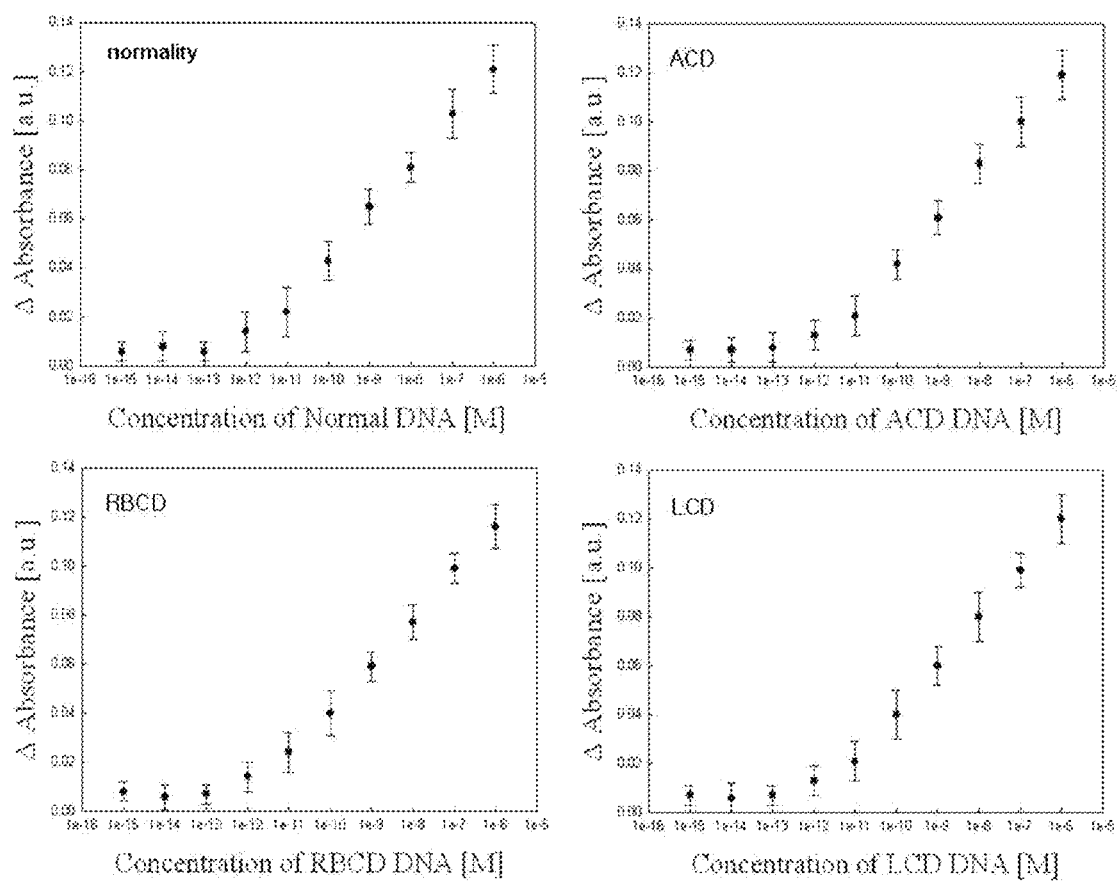
FIG. 6 shows the results of measuring the detection efficiency of a nucleic acid chip as a function of the concentration of each of normal target DNA and the target DNAs of Avellino corneal dystrophy (ACD), Reis-bucklers corneal dystrophy (RBCD) and lattice type I corneal dystrophy (LCD) using an LSPR optical property-based label-free optical biosensor comprising a multi-spot metal-capped nanostructure array nucleic acid chip for diagnosing corneal dystrophy according to the present invention.

Examination of Functionality of Nucleic Acid Chip as a Function of Concentration of Target DNA In the same manner as Example 7, using the LSPR optical property-based label-free optical biosensor comprising the multi-spot metal-capped nanostructure array nucleic acid chip constructed in Example 2, the detection efficiency of the nucleic acid chip according to the concentration of each of normal target DNA and the target DNAs of Avellino corneal dystrophy (ACD), lattice type I corneal dystrophy (LCD) and Reis-bucklers corneal dystrophy (RBCD) was measured. Each of the target DNAs was set within the range of 1 fM to 1 μM. Each of the probe DNAs having a length of 15 mer was immobilized on the surface of the nucleic acid, and each of the target DNAs having a length of 147 mer was allowed to react with each probe DNA at a humidity of 55% for 6 hours or more so as to induce complementary binding therebetween. As a result, as shown in FIG. 6, all the target DNAs could be analyzed with high sensitivity at a concentration of 1 pM, and the relationship between absorbance and the concentration of each target DNA was linear within the range of 1 pM to 1 μm. Thus, it was seen that the inventive multi-spot metal-capped nanostructure array nucleic acid chip for diagnosing corneal dystrophy can quantitatively analyze low concentrations of the target DNAs.

Example 9

Results of Hybridization of Nucleic Acid Chip for Application to Patient Diagnosis In order to prepare an efficient nucleic acid chip for diagnosing corneal dystrophy which can selectively detect a point mutation, in the same manner as Examples 7 and 8, the detection efficiency of the nucleic acid chip for selective detection of each of normal target DNA and the target DNAs of homozygous and heterozygous corneal dystrophies (ACD, RBCD, and LCD) was measured using the LSPR optical property-based label-free optical biosensor comprising the multi-spot metal-capped nanostructure array nucleic acid chip constructed in Example 2. The concentration of each of the target DNAs was set at 1 μM. Each of the probe DNAs having a length of 15 mer was immobilized to each spot point on the surface of the nucleic acid chip, and each of the target DNAs having a length of 147 mer was allowed to react at a humidity of 55% or higher for 6 hours or more, and the specific binding of each of complementary target DNAs and mismatch target DNAs was measured.

Figure 7:
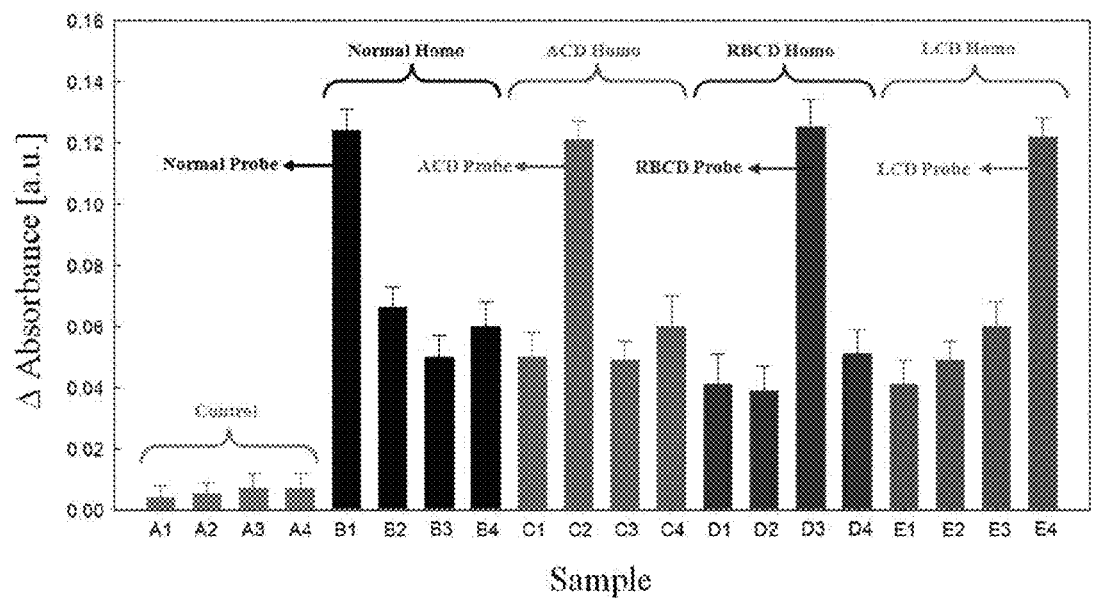
FIG. 7 shows the results of measuring the detection efficiency of the inventive nucleic acid chip for selective detection of each of normal target DNA and the target DNAs of homozygous and heterozygous corneal dystrophies (ACD, RBCD, and LCD) using an LSPR optical property-based label-free optical biosensor comprising the inventive multi-spot metal-capped nanostructure array nucleic acid chip for diagnosing corneal dystrophy.
Figure 8:
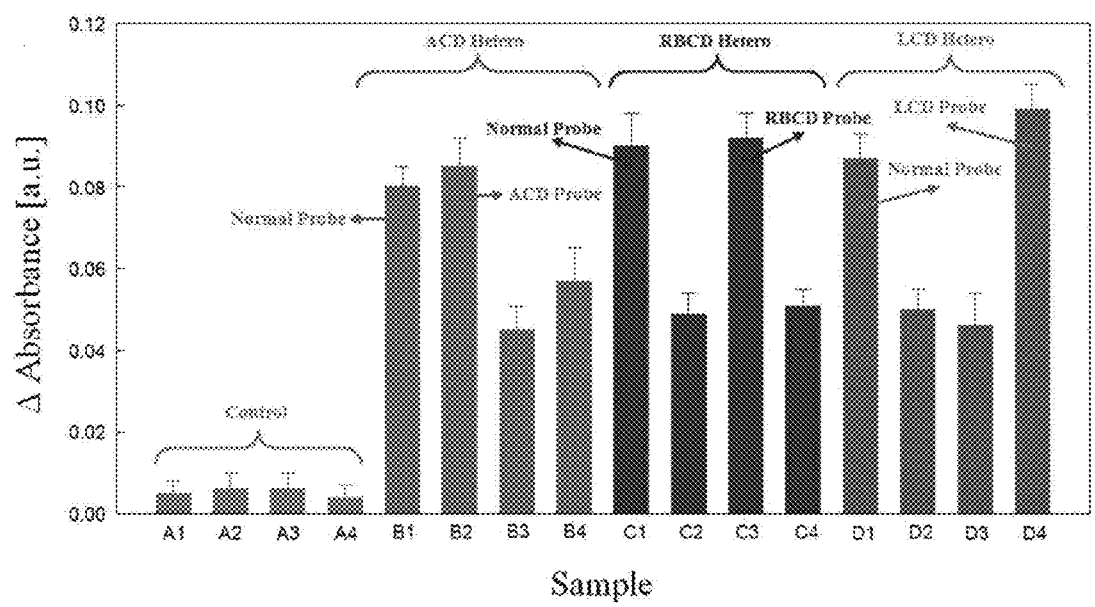
FIG. 8 shows the results of measuring the detection efficiency of the inventive nucleic acid chip for selective detection of each of normal target DNA and the target DNAs of homozygous and heterozygous corneal dystrophies (ACD, RBCD, and LCD) using an LSPR optical property-based label-free optical biosensor comprising the inventive multi-spot metal-capped nanostructure array nucleic acid chip for diagnosing corneal dystrophy.

FIGS. 7 and 8 show the results of measuring the efficiency of a nucleic acid chip for selective detection of each of normal target DNA and the target DNAs of homozygous and heterozygous corneal dystrophies (ACD, RBCD, and LCD) using the LSPR optical property-based label-free optical biosensor comprising the multi-spot metal-capped nanostructure array nucleic acid chip. As shown in FIGS. 7 and 8, complementary target DNAs and mismatch DNAs for all the target DNAs of homozygous and heterozygous corneal dystrophies could be selectively detected. Thus, it was found that the inventive multi-spot metal-capped nanostructure array nucleic acid chip for diagnosing corneal dystrophy could achieve multiple detections and selective analysis by one nucleic acid chip and that it could accurately diagnose all the applied patient samples.

INDUSTRIAL APPLICABILITY

As described above, the nucleic acid chip has the advantages of conventional metal-capped nanostructure array nucleic acid chips and can perform the multiple detections and quantitative analysis of BIGH3 gene mutations for diagnosing corneal dystrophies, including Avellino corneal dystrophy, which should be accurately diagnosed before sight correction surgery using LSPR optical properties. In addition, the nucleic acid chip of the present invention can be combined with analysis devices, including a light source, a detector, a spectrophotometer and a computer, to provide an LSPR optical property-based label-free optical biosensor, and can also be applied for on-site monitoring.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

What is claimed is:

1. A multi-spot metal-capped nanostructure array nucleic acid chip, comprising:
   (a) a substrate;
   (b) a first metal thin film layer formed on the substrate;
   (c) a nanostructure layer, including multi-spots formed on the first metal thin film layer, wherein nanostructures are arrayed on respective spot surfaces of the multi-spots at regular intervals;
   (d) a second metal thin film layer formed on the surface of the nanostructure layer; and
   (e) probe nucleic acids immobilized on the second metal thin film layer, wherein the probe nucleic acids are capable of detecting a plurality of target nucleic acids and the target nucleic acids in the plurality of target nucleic acids are each less than 190 nucleotides in length, wherein:
   the first metal thin film layer includes (i) a chromium thin film layer having a thickness of 5 nm on the substrate, (ii) a gold thin film layer having a thickness of 40 nm on the chromium thin film layer, and (iii) a self-assembly monolayer film of 4,4'-dithiodibutylic acid on the gold thin film layer;
   the nanostructures are silica nanostructures having a diameter of 100 nm and modified with 3-aminopropyltrioethoxysilane (γ-APTES) so that the silica nanostructures are covalently bound to the gold thin film layer;
   the second metal thin film layer is a gold thin film that has a thickness of 30 nm; and
   the probe nucleic acids are each 15 mers.

2. The multi-spot metal-capped nanostructure array nucleic acid chip according to claim 1, wherein the probe nucleic acids consist of a plurality of probe nucleic acids that recognize a plurality of target nucleic acids, and the probe nucleic acids include a sequence consisting of SEQ ID NO: 12.

3. The multi-spot metal-capped nanostructure array nucleic acid chip according to claim 1, wherein the probe nucleic acids comprise probe nucleic acids for detecting a BIGH3 gene mutation in the plurality of target nucleic acids.

4. The multi-spot metal-capped nanostructure array nucleic acid chip according to claim 3, wherein the probe nucleic acids for detecting a BIGH3 gene mutation comprising one or more sequences selected from the group consisting of SEQ ID NO: 11 to SEQ ID NO: 46.

5. The multi-spot metal-capped nanostructure array nucleic acid chip according to claim 1, including a porous mask immobilized on the first metal thin film layer.

6. The multi-spot metal-capped nanostructure array nucleic acid chip according to claim 5, wherein the porous mask is selected from the group consisting of a rubber flat plate, a silicon flat plate, and a mixture thereof.

7. The multi-spot metal-capped nanostructure array nucleic acid chip according to claim 1, wherein the probe nucleic acids include sequences consisting of SEQ ID NOs: 11-46.

* * * * *